US 9,788,960 B2

(12) United States Patent
Metz-Stavenhagen

(10) Patent No.: US 9,788,960 B2
(45) Date of Patent: Oct. 17, 2017

(54) SPINAL IMPLANTS AND RELATED APPARATUS AND METHODS

(71) Applicant: Peter Metz-Stavenhagen, Bad Wildungen (DE)

(72) Inventor: Peter Metz-Stavenhagen, Bad Wildungen (DE)

( * ) Notice: Subject to any disclaimer, the term of this patent is extended or adjusted under 35 U.S.C. 154(b) by 0 days.

(21) Appl. No.: 14/063,989

(22) Filed: Oct. 25, 2013

(65) Prior Publication Data

US 2014/0052249 A1 Feb. 20, 2014

Related U.S. Application Data

(63) Continuation of application No. PCT/DE2012/000392, filed on Apr. 13, 2012.

(30) Foreign Application Priority Data

Apr. 26, 2011 (DE) .................. 10 2011 018 692

(51) Int. Cl.
*A61F 2/44* (2006.01)
*A61F 2/46* (2006.01)
(Continued)

(52) U.S. Cl.
CPC ............ *A61F 2/44* (2013.01); *A61B 17/8872* (2013.01); *A61F 2/4611* (2013.01); *A61F 2/4465* (2013.01);
(Continued)

(58) Field of Classification Search
CPC .................. A61F 2/4455; A61F 2/4611; A61F 2002/4475; A61F 2002/4627;
(Continued)

(56) References Cited

U.S. PATENT DOCUMENTS

| 5,290,312 A | 3/1994 | Kojimoto et al. |
| 5,443,515 A | 8/1995 | Cohen et al. |

(Continued)

FOREIGN PATENT DOCUMENTS

| CN | 101474103 | 7/2009 |
| DE | 202004021288 | 6/2007 |

(Continued)

OTHER PUBLICATIONS

International Searching Authority, "International Preliminary Report on Patentability," issued in connection with application No. PCT/DE2012/000392, dated Oct. 29, 2013, 9 pages.

(Continued)

*Primary Examiner* — Ellen C Hammond
*Assistant Examiner* — Tessa Matthews
(74) *Attorney, Agent, or Firm* — Hanley, Flight & Zimmerman, LLC

(57) ABSTRACT

Example spinal implants and related apparatus and methods are disclosed. An example spinal implant includes an outer corpus and an inner corpus axially displaceably coupled to the outer corpus. A first lever accommodation is provided on the outer corpus and includes an elongated aperture. A first set of teeth are formed on a first side of the first lever accommodation. A second lever accommodation is provided on the inner corpus and includes an elongated aperture. A second set of teeth are formed on a second side of the second lever accommodation. The first and second lever accommodations are aligned. The example spinal implant includes a first guide on the inner corpus and a second guide on the outer corpus. The first and second guides allow for axial displacement of the inner corpus relative to the outer corpus and prevent rotation of the inner corpus relative to the outer corpus.

15 Claims, 4 Drawing Sheets

(51) Int. Cl.
*A61B 17/88* (2006.01)
*A61F 2/30* (2006.01)

(52) U.S. Cl.
CPC ............ *A61F 2002/3055* (2013.01); *A61F 2002/3069* (2013.01); *A61F 2002/30398* (2013.01); *A61F 2002/30426* (2013.01); *A61F 2002/30428* (2013.01); *A61F 2002/30507* (2013.01); *A61F 2002/30523* (2013.01); *A61F 2002/30601* (2013.01); *A61F 2002/30777* (2013.01)

(58) Field of Classification Search
CPC .. A61F 2002/30601; A61F 2002/30604; A61F 2002/30579; A61F 2/4425; A61F 2/446
USPC ............................................ 623/17.11, 17.16
See application file for complete search history.

(56) References Cited

U.S. PATENT DOCUMENTS

| | | | |
|---|---|---|---|
| 6,610,090 B1 | 8/2003 | Böhm et al. | |
| 6,752,832 B2 | 6/2004 | Neumann | |
| 6,902,579 B2 | 6/2005 | Harms et al. | |
| 7,029,498 B2 | 4/2006 | Boehm et al. | |
| 7,776,091 B2 | 8/2010 | Mastrorio et al. | |
| 7,918,891 B1 | 4/2011 | Curran et al. | |
| 8,182,535 B2 | 5/2012 | Kraus | |
| 8,273,126 B2 | 9/2012 | Lindner | |
| 8,337,558 B2 | 12/2012 | Lindner | |
| 8,357,181 B2 | 1/2013 | Lange et al. | |
| 8,585,763 B2 | 11/2013 | Olevsky et al. | |
| 8,685,100 B2 | 4/2014 | Jodaitis et al. | |
| 8,690,886 B2 | 4/2014 | Fedorov et al. | |
| 2002/0082695 A1 | 6/2002 | Neumann | |
| 2002/0082696 A1 | 6/2002 | Harms et al. | |
| 2003/0163199 A1 | 8/2003 | Boehm et al. | |
| 2006/0004376 A1 | 1/2006 | Shipp et al. | |
| 2006/0004447 A1 | 1/2006 | Mastrorio et al. | |
| 2006/0129238 A1 | 6/2006 | Paltzer | |
| 2006/0195096 A1 | 8/2006 | Lee et al. | |
| 2006/0241770 A1 | 10/2006 | Rhoda et al. | |
| 2007/0028710 A1 | 2/2007 | Kraus et al. | |
| 2007/0131070 A1 | 6/2007 | Hull et al. | |
| 2007/0191954 A1* | 8/2007 | Hansell et al. | 623/17.15 |
| 2007/0233098 A1 | 10/2007 | Mastrorio et al. | |
| 2008/0243254 A1* | 10/2008 | Butler | 623/17.16 |
| 2008/0288071 A1 | 11/2008 | Biyani et al. | |
| 2009/0012528 A1* | 1/2009 | Aschmann et al. | 606/99 |
| 2009/0112220 A1* | 4/2009 | Kraus | A61F 2/44 606/99 |
| 2009/0112320 A1 | 4/2009 | Kraus | |
| 2009/0192611 A1* | 7/2009 | Lindner | 623/17.11 |
| 2009/0192612 A1 | 7/2009 | Lindner | |
| 2010/0057204 A1 | 3/2010 | Kadaba et al. | |
| 2010/0100100 A1 | 4/2010 | Refai et al. | |
| 2010/0179594 A1 | 7/2010 | Theofilos et al. | |
| 2010/0274357 A1* | 10/2010 | Miller et al. | 623/17.16 |
| 2010/0298942 A1 | 11/2010 | Hansell et al. | |
| 2011/0178598 A1* | 7/2011 | Rhoda et al. | 623/17.16 |
| 2011/0251691 A1 | 10/2011 | McLaughlin et al. | |
| 2012/0179255 A1* | 7/2012 | DeFalco et al. | 623/17.11 |
| 2012/0203288 A1 | 8/2012 | Lange et al. | |
| 2013/0053965 A1 | 2/2013 | Metz-Stavenhagen | |
| 2013/0282120 A1* | 10/2013 | Refai et al. | 623/17.11 |

FOREIGN PATENT DOCUMENTS

| | | |
|---|---|---|
| DE | 102010018379 | 10/2011 |
| EP | 1219266 | 7/2002 |
| EP | 2055270 | 5/2009 |
| JP | 2008536649 | 9/2008 |
| WO | 2008121312 | 10/2008 |
| WO | 2009151734 | 12/2009 |
| WO | 2011134457 | 11/2011 |

OTHER PUBLICATIONS

International Searching Authority, "International Search Report," with English translation (pp. 6-8), issued in connection with application No. PCT/DE2012/000392, dated Sep. 4, 2012, 8 pages.

International Searching Authority, "Written Opinion of the International Searching Authority," issued in connection with application No. PCT/DE2012/000392, dated Sep. 4, 2012, 5 pages.

English Translation of Written Opinion of the International Searching Authority, issued by the International Searching Authority in connection with International Patent Application No. PCT/DE2011/000439, 5 pages.

English Translation of International Search Report, issued by the International Searching Authority in connection with International Patent Application No. PCT/DE2011/000439, 3 pages.

Non-Final Office Action, issued by the United States Patent and Trademark Office in connection with U.S. Appl. No. 13/660,644, dated Apr. 7, 2014, 38 pages.

Final Office Action, issued by the United States Patent and Trademark Office in connection with U.S. Appl. No. 13/660,644, dated Oct. 21, 2014, 29 pages.

United States Patent Office, Office Action issued in connection with U.S. Appl. No. 13/660,644 dated Jun. 12, 2015, 43 pages.

United States Patent and Trademark Office, "Final Office Action," issued in connection with U.S. Appl. No. 13/660,664 dated Feb. 17, 2016, 47 pages.

United States Patent and Trademark Office, "Advisory Action," issued in connection with U.S. Appl. No. 13/660,644, dated May 4, 2016, 41 pages.

English Machine Translation of German Language Office Action issued by the German Patent and Trademark Office in connection with German Patent Application No. DE10 2010 019 379.2-35 dated Dec. 21, 2010, 10 pages.

English Translation of "International Preliminary Report on Patentability", issued by the International Searching Authority in connection with International Patent Application No. PCT/DE2011/000439, dated Oct. 30, 2012, 6 pages.

English Translation of "Written Opinion of the International Searching Authority", issued by the International Searching Authority in connection with International Patent Application No. PCT/DE2012/000392, 8 pages.

United States Patent and Trademark Office, "Office Action," issued in connection with U.S. Appl. No. 13/660,644 dated Sep. 30, 2016 (25 pages).

United States Patent and Trademark Office, "Final Office Action," issued in connection with U.S. Appl. No. 13/660,644, dated May 18, 2017, 61 pages.

United States Patent and Trademark Office, "Advisory Action," issued in connection with U.S. Appl. No. 13/660,644, on Aug. 4, 2017, 4 pages.

* cited by examiner

SPINAL IMPLANTS AND RELATED APPARATUS AND METHODS

RELATED APPLICATIONS

This patent is a continuation of International Patent Application No. PCT/DE2012/000392, filed Apr. 13, 2012, which claims priority to German Patent Application No. 10 2011 018 692.1, filed Apr. 26, 2011, each of which is incorporated herein by reference in its entirety.

FIELD OF THE DISCLOSURE

The present invention relates generally to medical implants, and more specifically to spinal implants and related apparatus and methods.

BACKGROUND

A distractible spinal implant composed of two U-shaped parts is known from U.S. Pat. No. 7,029,498 B2 in which the two parts are held so that they are axially displaceable against each other in the manner of a telescope. On the free webs of the U-shaped outer part, a transport admission is formed, into which a gripping forceps is insertable. The attending physician can grasp the spinal implant with this gripping forceps and transport it to the desired location.

Once the spinal implant is positioned, the grasping forceps is removed. In order to distract the spinal implant to the desired size, an oblong guidance rod is then led past the opening of the U-shaped part into the inside of the spinal implant and screwed into a thread available on the outer part before pushing a hollow toothed instrument over the guidance rod. The toothed instrument is thereby pushed into the spinal implant until outer teeth provided on the toothed instrument engage with correspondingly formed teeth on the inner part of the spinal implant. If one now rotates the toothed instrument about its longitudinal axis, the inner part of the spinal implant is displaced relative to the outer part.

This entire process is very difficult and requires a high degree of dexterity on the part of the surgeon. Since the toothed instrument sits only very loosely on the guidance rod, it can happen that during distraction it accidentally slips out of the engagement with the teeth, so that it needs to be inserted again.

DETAILED DESCRIPTION

Figure 1:
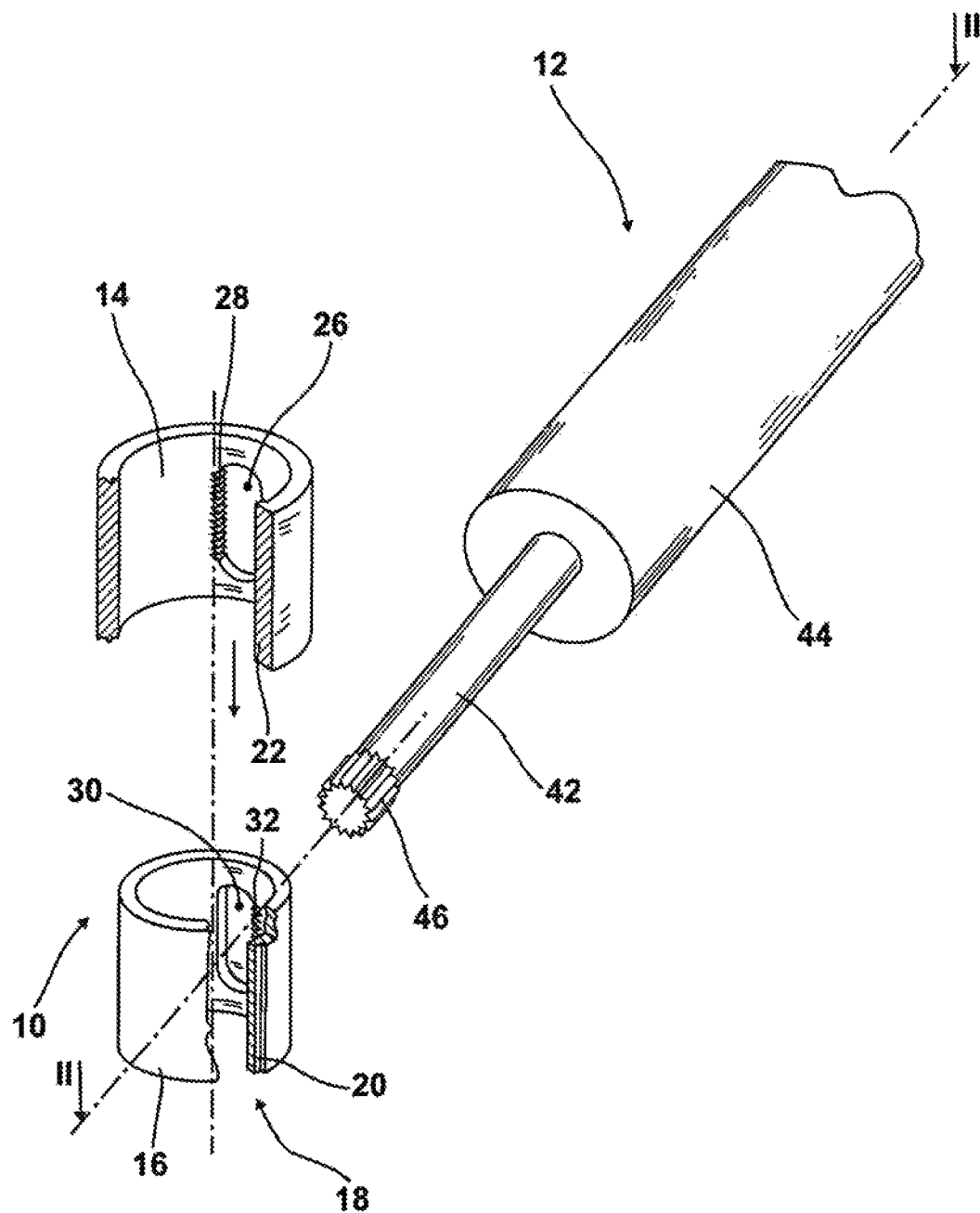
FIG. 1 shows a perspective representation of an example spinal implant according to the teachings of this disclosure and of an example tool according to the teachings of this disclosure.

One object of the present disclosure is to develop a spinal implant and a tool for this purpose of increased positionability and stability, so that the spinal implant can be easily and precisely implanted and distracted.

As a technical solution to this object, example spinal implants and related apparatus and methods of the type claimed are proposed. Advantageous implementations of these example spinal implants, example apparatus and tools, and example methods can be gathered from the respective sub-claims.

A spinal implant configured according to this technical teaching has the advantage that due to the opposite movement of the inner and outer corpuses a quick distraction is achieved because both corpuses can be moved simultaneously with one movement of the hand.

Another advantage is that a precise adjustment of the spinal implant is achieved due to the comparatively great range.

Yet another advantage is that due to the positive-fit engagement of the tool with the wall toothing, it is also possible to distract the inner corpus or the outer corpus with little effort, even when it has already been implanted and even when it is loaded.

This two-part implementation of the tool has the advantage that the inner corpus and/or the outer corpus can be very precisely moved. This makes it possible for the attending physician to move only the inner corpus or only the outer corpus depending on each situation.

In some examples, guidance means are provided on the inner and on the outer corpus, which prevent torsion of the inner corpus relative to the outer corpus and simultaneously ensure an axial guidance. This is has the advantage that circumferential forces, which may occur during distraction, do not lead to torsion of the inner corpus.

In some examples, the guidance means are configured according to the tongue and groove principle. Thereby, a coaxially disposed groove is formed, for example, in the inner corpus, into which a correspondingly formed protrusion on the inner wall of the outer corpus engages. As a result of this tongue and groove construction, the guidance of the inner corpus occurs along a certain length of the spinal implant, thereby reliably preventing a jamming.

Other advantages of the spinal implant disclosed herein, of the example apparatus and tools disclosed herein, and of the example methods disclosed herein can be gathered from the enclosed drawings and the embodiments described in the following. According to the disclosure, the aforementioned features as well as features that will be further described can be respectively used individually or in any combination. The mentioned embodiments are not to be understood as an exhaustive list but merely as examples.

Some example spinal implant disclosed herein include an outer corpus and an inner corpus axially displaceably coupled to the outer corpus. The example spinal implant also includes a first lever accommodation provided on the outer corpus. The first lever accommodation includes an elongated aperture and a first set of teeth formed on a first longitudinal side of the first lever accommodation and protruding into the first lever accommodation. The example implant also includes a second lever accommodation provided on the inner corpus. The second lever accommodation includes an elongated aperture and a second set of teeth formed on a second longitudinal side of the second lever accommodation and protruding into the second lever accommodation. In this example, the first lever accommodation and the second lever accommodation are aligned so that the first longitudinal side is opposite the second longitudinal side. The example implant also includes a first guide provided on the inner corpus and a second guide provided on the outer corpus. The first guide and the second guide to allow for axial displacement of the inner corpus relative to the outer corpus and to prevent rotation of the inner corpus relative to the outer corpus.

In some examples, one of the first guide or the second guide includes a tongue and the other one of the first guide or the second guide comprises a groove.

Also disclosed herein is a tool for use with the example spinal implant described above. The example tool includes a handle and a lever coupled to the handle. The lever includes an inner rotator, which includes a tooth coupled to an end of the inner rotator. The example lever also includes an outer rotator, which includes a tooth coupled to an end of the outer rotator the inner rotator to be used independently from the outer rotator.

In some examples, the handle includes a first handle and a second handle, and the inner rotator coupled to the first handle and the outer rotator are coupled to the outer handle.

In some examples, a length of the inner tooth is substantially the same as a length of the outer tooth.

Also disclosed herein is an example method for distracting a spinal implant. The example method includes inserting a tool into a spinal implant. The tool includes a lever having an inner rotator and an outer rotator. The spinal implant includes an inner corpus having a first lever accommodation and an outer corpus having second lever accommodation. Inserting the tool into the spinal implant includes engaging a set of teeth of the inner rotator with a set of teeth of the second lever accommodation and engaging a set of teeth of the outer rotator with a set of teeth of the first lever accommodation. The example method also includes rotating at least one of the inner rotator or the outer rotator to distract the spinal implant.

In some examples, the example method also includes actuating the inner rotator by rotating a first handle of the tool about a longitudinal axis of the first handle, where the inner rotator coupled to the first handle. Additionally or alternatively, some example methods include actuating the outer rotator by rotating a second handle of the tool about longitudinal axis of the second handle, where the outer rotator coupled to the second handle.

Also disclosed herein is an example spinal implant with an outer corpus and with an axially displaceable inner corpus held therein. A first lever accommodation is provided on the outer corpus, and a second lever accommodation is provided on the inner corpus. In some examples, both lever accommodations are configured as a long hole, and both lever accommodations are disposed so that they are flush relative to each other. In some examples, a number of wall teeth protruding into the lever accommodation are formed on the longitudinal side of the first and second lever accommodations, and the wall teeth are disposed on opposite sides in their respective lever accommodation.

In some examples, the implant includes guidance means on the inner corpus and on the outer corpus, which allow for an axial displacement of the inner corpus relative to the outer corpus but which prevent a twisting of the inner corpus relative to the outer corpus.

In some examples, the guidance means are configured according to a tongue and groove principle.

Also disclosed herein are tools for use with an implant. An example tool includes a rod-like lever-rotator and a handle attached thereto. In some such examples, the lever-rotator has a plurality of teeth distributed along the circumference at its distal end, each tooth is oriented coaxially. In some examples, each tooth is configured so long that it can simultaneously engage with a corresponding wall tooth of a first lever accommodation and with a corresponding wall tooth of a second lever accommodation of the example spinal implant.

In some examples, an example tool includes a rod-like lever-rotator and a handle attached thereto, and the lever-rotator is implemented in two parts. In some such examples, the lever rotator includes an inner rotator and an outer rotator. The inner rotator includes an inner tooth at its distal end, and the outer rotator includes an outer tooth at its distal end, so that the inner rotator can be used independently from the outer rotator.

In some examples, the handle is implemented in two parts. In some such examples, the handle includes an inner handle and an outer handle. The inner rotator is actively connected with the inner handle, and the outer rotator is actively connected with the outer handle.

In some examples, the inner tooth and the outer tooth have the same length.

Also disclosed herein are example methods of implementing the example implants and example tools disclosed herein. In an example method, the tool is inserted with the lever rotator into the two lever accommodations on the inner corpus and the outer corpus of the spinal implant in such a manner that the lever rotator is engaged with the teeth in the wall teeth of the two lever accommodations before the spinal implant is distracted by rotation of the lever-rotator about its longitudinal axis.

In some examples, the tool is first inserted with its lever-rotator into the two lever accommodations in the inner corpus and the outer corpus of the spinal implant in such a manner that the inner rotator is engaged with its inner teeth in the wall teeth of the lever accommodation of the outer corpus. The outer rotator is engaged with its outer teeth in the wall teeth of the lever accommodation of the inner corpus before the spinal implant is distracted by rotation either of the inner rotator or of the outer rotator or both.

In some examples, the inner rotator is actuated by rotation of the inner handle about its longitudinal axis and/or that the outer rotator is actuated by rotation of the outer handle about its longitudinal axis.

Figure 2:
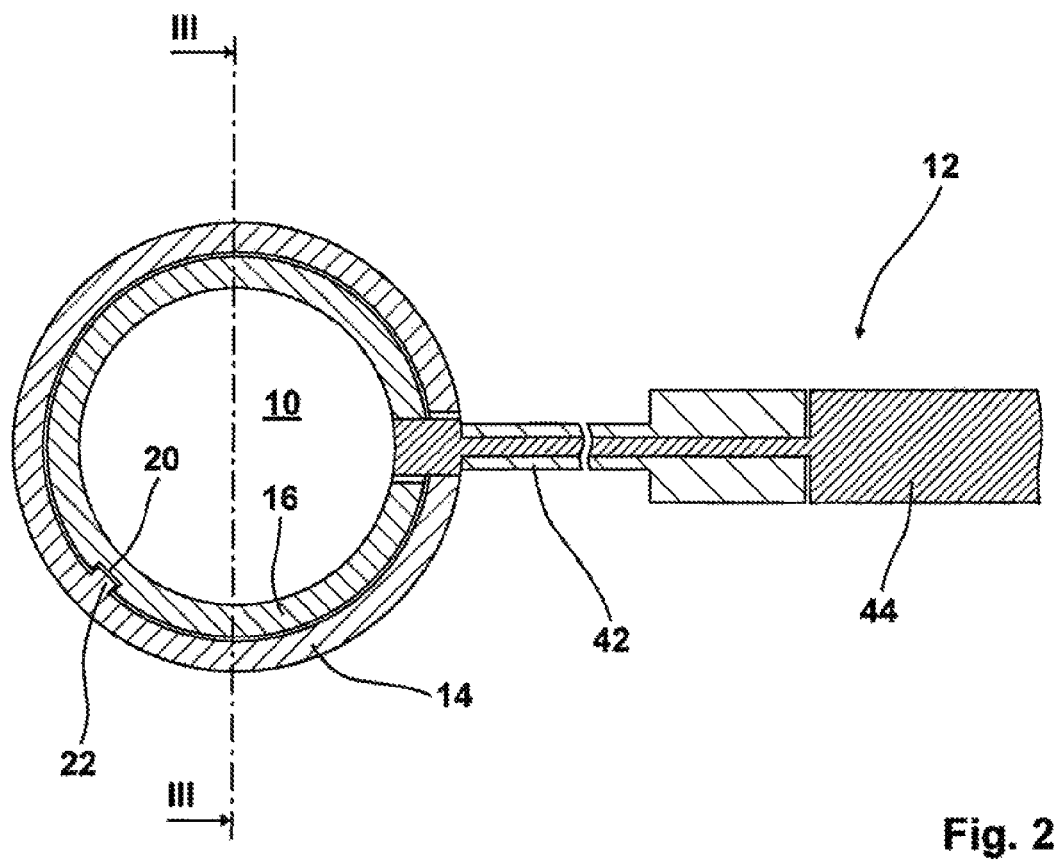
FIG. 2 shows a cross-sectional view from above of the example spinal implant and the tool of FIG. 1, cut along the line II-II in FIG. 1.
Figure 3:
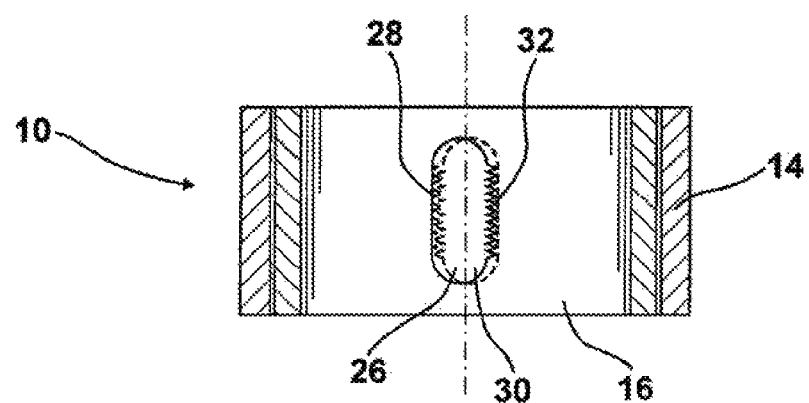
FIG. 3 shows a cross-sectional view of the example spinal implant of FIG. 1, cut along the line III-III in FIG. 2.

Turning now to the figures, an example spinal implant 10 and a first example tool 12 are shown in FIGS. 1 to 3.

The example spinal implant 10 comprises an outer corpus 14 and an axially displaceable inner corpus 16. In the present example, both corpuses are cylindrical. Guidance means 18 are arranged on both corpuses 14, 16 to guide the axial movement of the corpuses 14, 16 and to prevent twisting of the corpuses 14, 16 relative to each other. The guidance means 18 includes a coaxially oriented groove 20 embedded on an outer side of the inner corpus 16 and a protrusion 22 formed on the inner side of the outer corpus 14 such that the protrusion 22 corresponds to the groove 20.

A first lever accommodation 26 is formed as a coaxially oriented long hole along the inner corpus 16. A number of wall teeth 28 are formed on a right or left vertical flank of first lever accommodation 26. A second lever accommodation 30 is formed as a coaxially oriented long hole along the outer corpus 14. A number of wall teeth 32 are formed on a right or left vertical flank of the second lever accommodation 28. In some examples, the respective wall teeth 28, 32 of the first and second lever accommodations 26, 30 are provided on opposite flanks of the respective first and second lever accommodations 26, 30.

The groove 20, the protrusion 22, the inner corpus 16 and the outer corpus 14 are disposed in such a manner that the first lever accommodation 26 formed as a long hole is at least partially flush with the second lever accommodation 30 formed as a long hole, so that the tool 12 can be inserted through the second lever accommodation 30 into the first lever accommodation 26.

The first example tool 12 includes a rod-type lever-rotator 42 having a handle 44 attached thereto. At the distal end of the lever-rotator 42, a number of radially protruding teeth 46 are provided, which are formed on a surface coaxial to the longitudinal axis of the lever-rotator 42. In some examples, the teeth 46 are arranged to form a toothed ring. Also, in some examples, a respective tooth 46 can engage simultaneously with a corresponding wall tooth 48 of the first lever accommodation 26 and into a corresponding wall tooth 32 of the second lever accommodation 30 of the spinal implant 10.

Figure 4:
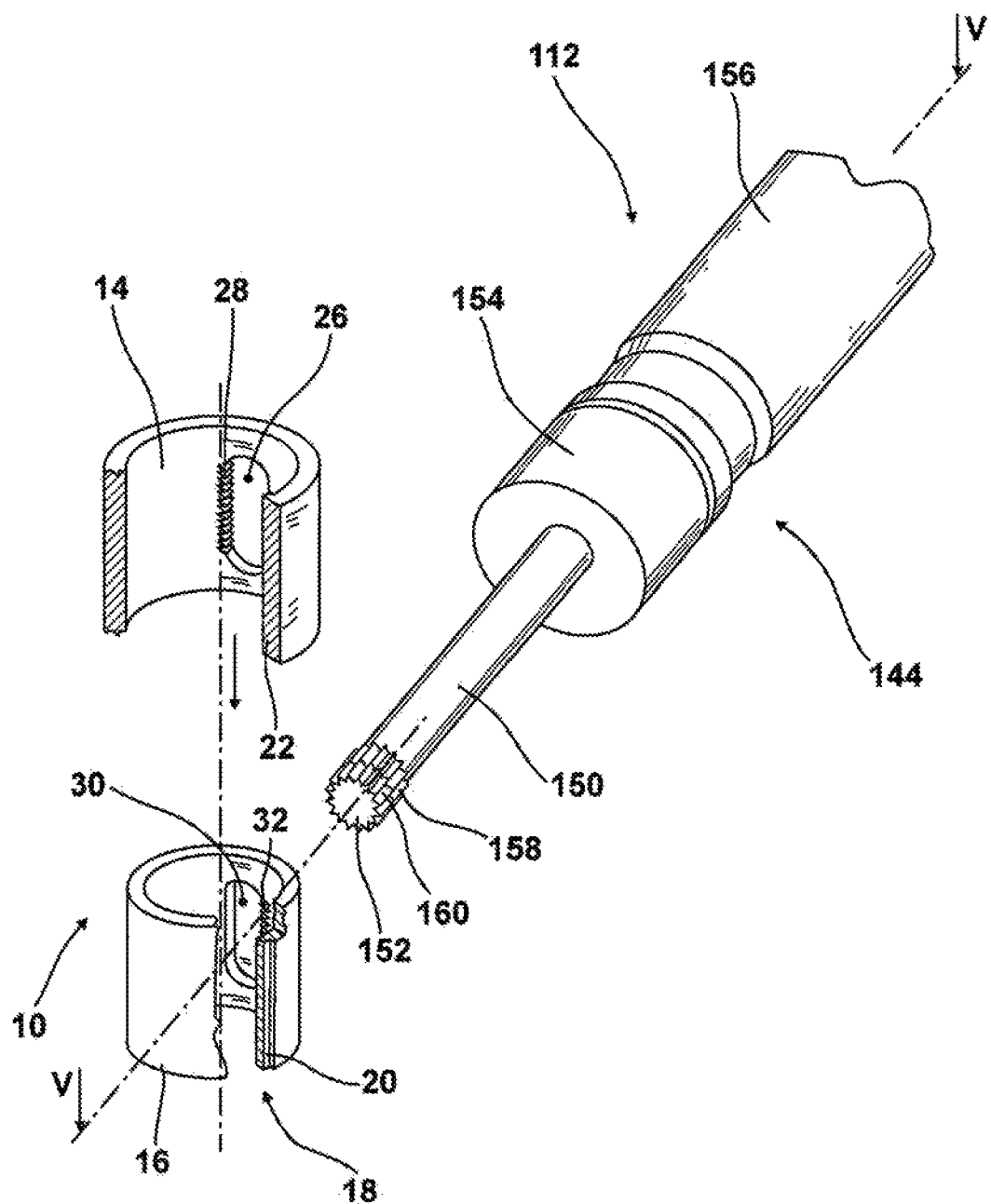
FIG. 4 shows a perspective representation of the example spinal implant of FIG. 1 and of a second example of a tool according to the teachings of this disclosure.
Figure 5:
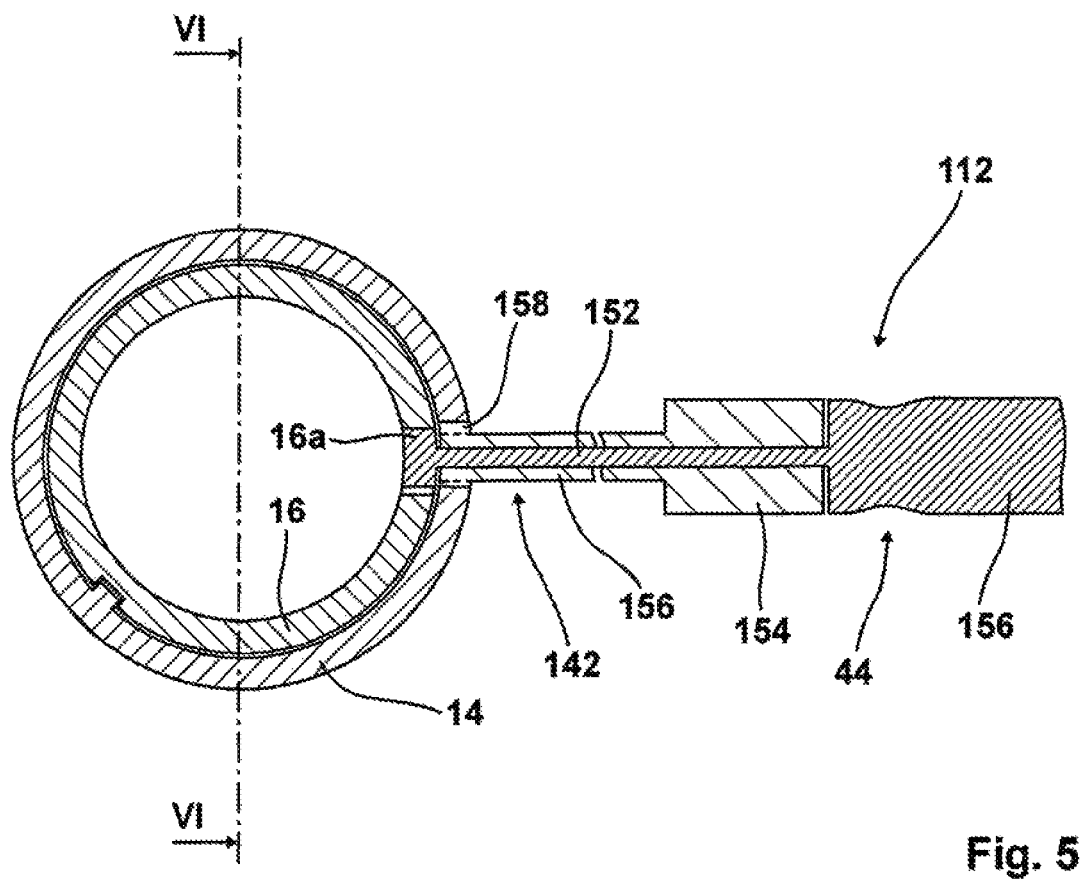
FIG. 5 shows a cross-sectional view from above of the example spinal implant of FIG. 1 and of the example of FIG. 4.
Figure 6:
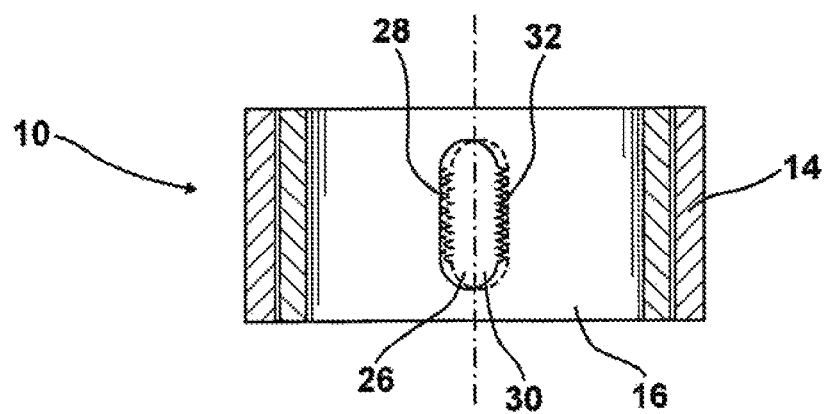
FIG. 6 shows a cross-sectional view from above of the spinal implant of FIG. 1, cut along the line VI-VI in FIG. 5.

A second example tool 112 is shown in FIGS. 4 to 6. The second example tool 112 differs from the first example tool 12 shown in FIGS. 1 to 3 in that the lever rotator 142 of the second example tool 112 of FIGS. 4 to 6 is formed by two parts and has an inner rotator 150 and an outer rotator 152. Also, in the second example tool 112, the handle 144 is divided in two and includes an inner handle 154 and an outer handle 156.

The inner rotator 150 is actively connected to the inner handle 154 and the outer handle 156 is actively connected to the outer rotator 152, so that the inner rotator 150 can be actuated by way of the inner handle 154 and the outer rotator 152 can be actuated by way of the outer handle 156. Thereby both the inner rotator 150 and the outer rotator 152 can be used independently. To this end, the inner rotator 150 and the inner handle 154 are configured to include a hollow space so that the outer rotator 152 is held in the hollow space.

Inner teeth 158 and outer teeth 160, which both, in some examples, have the same length, are disposed at the distal end of the inner rotator 150 and at the distal end of the outer rotator 152 so as to protrude radially.

During a surgical operation, the attending physician determines the size of the spinal implant 10 to be used. The spinal implant 10 is then inserted into the body at the desired location. For distraction, the first example tool 12 of FIGS. 1 to 3 is then inserted into the spinal implant in such a manner that the teeth 46 extend into the first lever accommodation 26 as well as into the second lever accommodation 30 and engage the wall teeth 28, 32. The attending physician then rotates the handle 44 of the first example tool 12 around its longitudinal axis. The lever-rotator 42 thereby causes a displacement of the inner corpus 16 in one direction and a displacement of the outer corpus 14 in the other direction. Since both corpuses 14 and 16 can be moved with one single hand movement, the distraction can be implemented very quickly and very precisely.

When using the second example tool 112 according to FIGS. 4 to 6, the outer teeth 160 engage with the first lever accommodation 26 in the inner corpus 16 and the inner teeth 158 engage with the second lever accommodation 30 in the outer corpus 14. By rotating the inner handle 154, the outer corpus 14 can now be moved axially. Additionally or alternatively, by rotating the outer handle 156, the inner corpus 16 can be moved axially.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A spinal implant comprising:
   an outer corpus including a first surface and a second surface;
   an inner corpus including a third surface and a fourth surface, the inner corpus axially displaceably coupled to the outer corpus, the third surface of the inner corpus surrounded by the second surface of the outer corpus;
   a first lever accommodation provided on the outer corpus, the first lever accommodation comprising an elongated aperture that includes:
      a first longitudinal side having a first set of teeth protruding into the first lever accommodation, the first set of teeth formed between the first surface and the second surface, wherein the first set of teeth extend from the first surface to the second surface; and
      a substantially smooth second longitudinal side;
   a second lever accommodation provided on the inner corpus, the second lever accommodation comprising an elongated aperture that includes:
      a first longitudinal side; and
      a second longitudinal side having a second set of teeth protruding into the second lever accommodation, the second set of teeth formed between the third surface and the fourth surface, wherein the first lever accommodation and the second lever accommodation are aligned so that the first longitudinal side of the first lever accommodation is opposite the second longitudinal side of the second lever accommodation;
   a first guide provided on the inner corpus; and
   a second guide provided on the outer corpus, the first guide and the second guide to allow for axial displacement of the inner corpus relative to the outer corpus and to prevent rotation of the inner corpus relative to the outer corpus.

2. A tool for the spinal implant according to claim 1, the tool comprising:
   a handle;
   a lever coupled to the handle, the lever comprising:
      an inner rotator, the inner rotator comprising a tooth coupled to an end of the inner rotator; and
      an outer rotator, the outer rotator comprising a tooth coupled to an end of the outer rotator, the inner rotator to be used independently from the outer rotator.

3. The tool according to claim 2, wherein the handle comprises a first handle and a second handle, the inner rotator coupled to the first handle and the outer rotator coupled to the second handle.

4. The tool according to claim 2, wherein a length of the tooth of the inner rotator is substantially the same as a length of the tooth of the outer rotator.

5. The tool according to claim 2, wherein the inner rotator is to be independently rotatable relative to the outer rotator.

6. The tool according to claim 2, wherein the tooth of the inner rotator is to engage the first lever accommodation at substantially the same time the tooth of the outer rotator is to engage the second lever accommodation.

7. The spinal implant according to claim 1, wherein the first longitudinal side of the second lever accommodation is substantially smooth.

8. The spinal implant according to claim 1, wherein the first lever accommodation and the second lever accommodation are aligned along respective parallel planes.

9. The spinal implant according to claim 1, wherein the second lever accommodation is slidable relative to the first lever accommodation.

10. The spinal implant according to claim 1, wherein the first lever accommodation is disposed at a first distance from a center of the spinal implant and the second lever accommodation is disposed at a second distance from the center, the second distance less than the first distance.

11. The spinal implant according to claim 1, wherein each of the first surface, the second surface, the third surface, the fourth surface, the first longitudinal side of the first lever accommodation, and the second longitudinal side of the second lever accommodation extend longitudinally along a central axis passing through the outer corpus and the inner corpus.

12. The spinal implant according to claim 1,
wherein the elongated aperture of the first lever accommodation includes a third side and a fourth side opposite the third side, each of the third side and the forth side extending between the first longitudinal side and the second longitudinal side of the first lever accommodation; and
wherein the elongated aperture of the second lever accommodation includes a third side and a fourth side opposite the third side, each of the third side and the forth side extending between the first longitudinal side and the second longitudinal side of the second lever accommodation.

13. The spinal implant according to claim 1, wherein the second surface and the third surface are radially aligned about a central axis passing through the outer corpus and the inner corpus.

14. The spinal implant according to claim 1, wherein one of the first guide or the second guide comprises a tongue and the other one of the first guide or the second guide comprises a groove.

15. A spinal implant comprising:
an outer corpus including a first surface and a second surface;
an inner corpus including a third surface and a fourth surface, the inner corpus axially displaceably coupled to the outer corpus, the third surface of the inner corpus surrounded by the second surface of the outer corpus;
a first lever accommodation provided on the outer corpus, the first lever accommodation comprising an elongated aperture that includes:
a first longitudinal side having a first set of teeth protruding into the first lever accommodation, the first set of teeth formed between the first surface and the second surface, wherein the first set of teeth extend from the first surface to the second surface, and wherein at least a portion of the respective teeth of the first set of teeth extend perpendicular to the first surface and the second surface; and
a substantially smooth second longitudinal side;
a second lever accommodation provided on the inner corpus, the second lever accommodation comprising an elongated aperture that includes:
a first longitudinal side; and
a second longitudinal side having a second set of teeth protruding into the second lever accommodation, the second set of teeth formed between the third surface and the fourth surface, wherein the first lever accommodation and the second lever accommodation are aligned so that the first longitudinal side of the first lever accommodation is opposite the second longitudinal side of the second lever accommodation;
a first guide provided on the inner corpus; and
a second guide provided on the outer corpus, the first guide and the second guide to allow for axial displacement of the inner corpus relative to the outer corpus and to prevent rotation of the inner corpus relative to the outer corpus.

* * * * *